United States Patent
Buysse et al.

(10) Patent No.: US 10,194,934 B2
(45) Date of Patent: Feb. 5, 2019

(54) ACTIVE COOLING SYSTEM AND APPARATUS FOR CONTROLLING TEMPERATURE OF A FLUID USED DURING TREATMENT OF BIOLOGICAL TISSUE

(71) Applicant: COVIDIEN LP, Mansfield, MA (US)

(72) Inventors: Steven P. Buysse, Niwot, CO (US);
David N. Heard, Boulder, CO (US)

(73) Assignee: Covidien LP, Mansfield, MA (US)

(*) Notice: Subject to any disclaimer, the term of this patent is extended or adjusted under 35 U.S.C. 154(b) by 424 days.

(21) Appl. No.: 14/192,293

(22) Filed: Feb. 27, 2014

(65) Prior Publication Data

US 2014/0180266 A1 Jun. 26, 2014

Related U.S. Application Data

(63) Continuation of application No. 12/507,895, filed on Jul. 23, 2009, now Pat. No. 8,672,938.

(51) Int. Cl.
*A61B 18/08* (2006.01)
*A61B 17/3203* (2006.01)
(Continued)

(52) U.S. Cl.
CPC ........ *A61B 17/3203* (2013.01); *A61B 18/082* (2013.01); *G05D 23/19* (2013.01); *A61B 2018/00011* (2013.01)

(58) Field of Classification Search
CPC ... A61B 18/02; A61B 18/0218; A61B 18/082; A61B 2018/00011; A61B 2018/00005;
(Continued)

(56) References Cited

U.S. PATENT DOCUMENTS 4,827,911 A 5/1989 Broadwin et al.
4,931,047 A 6/1990 Broadwin et al.
(Continued)

FOREIGN PATENT DOCUMENTS

EP 310431 A2 4/1989
EP 1977709 A1 10/2008
(Continued)

OTHER PUBLICATIONS

"Cooler Dialysis Fluids May Help with Insomnia and Fatigue" New York Times, p. F8, Apr. 3, 2007.

*Primary Examiner* — Ronald Hupczey, Jr.
*Assistant Examiner* — Khadijeh Vahdat

(57) ABSTRACT

A system for controlling temperature of a fluid used during treatment of biological tissue includes a fluid temperature control apparatus. The apparatus includes at least one heat transfer device and a solution bag and/or a heat transfer membrane. The solution bag and/or the heat transfer membrane reside in thermal communication with the heat transfer device. When the solution bag and/or the heat transfer membrane is fluidically coupled to an electrosurgical device, fluid is supplied to the electrosurgical device at a controlled temperature during a surgical procedure utilizing the electrosurgical device to enable more efficient treatment of the biological tissue. A corresponding method includes fluidically coupling the fluid temperature control apparatus to the electrosurgical device and supplying fluid at a controlled temperature during a surgical procedure utilizing the electrosurgical device to enable more efficient treatment of the biological tissue.

10 Claims, 11 Drawing Sheets

(51) Int. Cl.
*G05D 23/19* (2006.01)
*A61B 18/00* (2006.01)

(58) Field of Classification Search
CPC .......... A61B 2018/00023; A61B 2018/00035; A61B 2018/025; A61B 2018/0262; A61B 17/3202; G05D 23/19
USPC ...................................................... 606/21–26
See application file for complete search history.

(56) References Cited

U.S. PATENT DOCUMENTS

| | | | |
|---|---|---|---|
| 5,015,227 A | 5/1991 | Broadwin et al. | |
| 5,139,496 A * | 8/1992 | Hed | A61B 18/0206 606/21 |
| 5,486,183 A | 1/1996 | Middleman et al. | |
| 5,810,804 A | 9/1998 | Gough et al. | |
| 5,837,003 A * | 11/1998 | Ginsburg | A61F 7/12 606/27 |
| 6,019,783 A * | 2/2000 | Philips | A61F 7/12 606/21 |
| 6,059,780 A | 5/2000 | Gough et al. | |
| 6,355,024 B1 | 3/2002 | Small et al. | |
| 6,413,255 B1 | 7/2002 | Stern | |
| 6,425,912 B1 | 7/2002 | Knowlton | |
| 6,440,158 B1 | 8/2002 | Saab | |
| 6,506,189 B1 | 1/2003 | Rittman, III et al. | |
| 6,524,308 B1 | 2/2003 | Muller et al. | |
| 6,537,272 B2 | 3/2003 | Christopherson et al. | |
| 6,702,810 B2 | 3/2004 | McClurken et al. | |
| 6,818,000 B2 | 11/2004 | Muller et al. | |
| 6,849,073 B2 | 2/2005 | Hoey et al. | |
| 6,905,510 B2 | 6/2005 | Saab | |
| 6,932,816 B2 | 8/2005 | Phan | |
| 6,942,661 B2 | 9/2005 | Swanson | |
| 6,953,461 B2 | 10/2005 | McClurken et al. | |
| 7,169,144 B2 | 1/2007 | Hoey et al. | |
| 7,175,621 B2 | 2/2007 | Heim et al. | |
| 7,217,282 B2 | 5/2007 | Ginsburg et al. | |
| 7,247,155 B2 | 7/2007 | Hoey et al. | |
| 7,282,051 B2 | 10/2007 | Rioux et al. | |
| 7,303,558 B2 | 12/2007 | Swanson | |
| 7,306,592 B2 | 12/2007 | Morgan et al. | |
| 7,387,625 B2 | 6/2008 | Hovda et al. | |
| 7,400,930 B2 | 7/2008 | Sharkey et al. | |
| 7,425,212 B1 | 9/2008 | Danek et al. | |
| 7,468,059 B2 | 12/2008 | Eggers et al. | |
| 7,850,723 B1 * | 12/2010 | Magers | A61B 5/048 607/105 |
| 8,672,938 B2 | 3/2014 | Buysse et al. | |
| 2001/0021847 A1 * | 9/2001 | Abboud | A61B 18/02 606/21 |
| 2002/0173834 A1 * | 11/2002 | Noda | A61F 7/12 607/105 |
| 2003/0114850 A1 | 6/2003 | McClurken et al. | |
| 2003/0158549 A1 | 8/2003 | Swanson | |
| 2005/0033278 A1 | 2/2005 | McClurken et al. | |
| 2005/0059966 A1 | 3/2005 | McClurken et al. | |
| 2005/0065584 A1 | 3/2005 | Schiff et al. | |
| 2006/0116675 A1 | 6/2006 | McClurken et al. | |
| 2007/0016182 A1 | 1/2007 | Lipson et al. | |
| 2007/0027449 A1 | 2/2007 | Godara et al. | |
| 2007/0073285 A1 | 3/2007 | Peterson | |
| 2007/0078453 A1 | 4/2007 | Johnson et al. | |
| 2007/0078454 A1 | 4/2007 | McPherson | |
| 2007/0135812 A1 | 6/2007 | Sartor | |
| 2007/0179497 A1 | 8/2007 | Eggers et al. | |
| 2007/0260235 A1 | 11/2007 | Podhajsky | |
| 2007/0293855 A1 | 12/2007 | Sliwa et al. | |
| 2008/0027424 A1 | 1/2008 | DeCarlo et al. | |
| 2008/0114344 A1 * | 5/2008 | Xiao | A61B 18/02 606/20 |
| 2008/0249521 A1 | 10/2008 | Dunning et al. | |
| 2008/0287946 A1 | 11/2008 | DeCarlo et al. | |

FOREIGN PATENT DOCUMENTS

| | | |
|---|---|---|
| EP | 1977710 A1 | 10/2008 |
| WO | 96/34571 A1 | 11/1996 |
| WO | 97/06739 A2 | 2/1997 |
| WO | 00/53113 A1 | 9/2000 |

* cited by examiner

ACTIVE COOLING SYSTEM AND APPARATUS FOR CONTROLLING TEMPERATURE OF A FLUID USED DURING TREATMENT OF BIOLOGICAL TISSUE

CROSS-REFERENCE TO RELATED APPLICATION

The present application is a continuation application of U.S. application Ser. No. 12/507,895, filed Jul. 23, 2009, now U.S. Pat. No. 8,672,938, the entire contents of which are incorporated by reference herein.

BACKGROUND

1. Technical Field

The present disclosure relates to cooling of fluids used during treatment of biological tissue.

2. Discussion of Related Art

When using energy, e.g., radiofrequency (RF) waves, microwave (MW) or ultrasonic (US) waves to treat tissue, high temperatures around the electrode-tissue interface lead to increased resistance to the deposition of more energy (RF impedance, MW reflectance) because of dessication of patient tissue followed by charring around the electrode tip. The dessication and charring lead to a reduction in current and a reduction in the amount of energy transferred and a reduction in heating of the tissue. Methods of cooling of fluid used to cool the tissue and the electrode-tissue interface are known in the art, e.g., pouches of saline solution are maintained in ice baths. However, such methods do not provide efficient temperature control necessary to maximize energy transfer while minimizing overdessication of the tissue. In addition, such methods require pre-chilling of the fluid prior to the ablation treatment.

SUMMARY

The present disclosure relates to systems and methods for consistent cooling of fluids used during biological treatment of tissue. In particular, the present disclosure includes in one embodiment an apparatus for controlling temperature of a fluid used during treatment of biological tissue. The apparatus includes at least one heat transfer device; a solution bag and/or at least one heat transfer membrane residing in thermal communication with the at least one heat transfer device; and a fluid conduit defining a path through the one or more heat transfer surfaces of the one or more heat transfer membranes The fluid conduit is configured to enable heat transfer across the one or more heat transfer surfaces of the one or more heat transfer membranes upon flow of fluid through the fluid conduit in the path when the one or more heat transfer membranes are configured to fluidically couple to an electrosurgical device. The solution bag and/or the one or more heat transfer membranes resides in thermal communication with the one or more heat transfer devices, and the solution bag and/or the one or more heat transfer membranes fluidically couples to an electrosurgical device to supply fluid thereto.

The present disclosure includes in one embodiment a system for controlling temperature of a fluid used during treatment of biological tissue. The system includes a fluid temperature control apparatus that includes at least one heat transfer device; and a solution bag and/or at least one heat transfer membrane. The solution bag and/or the one or more heat transfer membranes resides in thermal communication with the one or more heat transfer devices. The solution bag and/or the one or more heat transfer membranes fluidically couples to an electrosurgical device to supply fluid at a controlled temperature during a surgical procedure.

The present disclosure includes in one embodiment a method for controlling temperature of a fluid used during treatment of biological tissue. The method includes the steps of fluidically coupling a fluid temperature control apparatus to an electrosurgical device to supply fluid thereto; and supplying fluid to the electrosurgical device at a controlled temperature during a surgical procedure utilizing the electrosurgical device to enable more consistent treatment of the biological tissue.

BRIEF DESCRIPTION OF THE DRAWINGS

Various embodiments of the present disclosure are described herein with reference to the drawings wherein.

DETAILED DESCRIPTION

The present disclosure relates to systems and methods for consistent cooling of fluids used during biological treatment of tissue to advance the state of the art of biological treatment of tissue as described above.

Figure 1A:
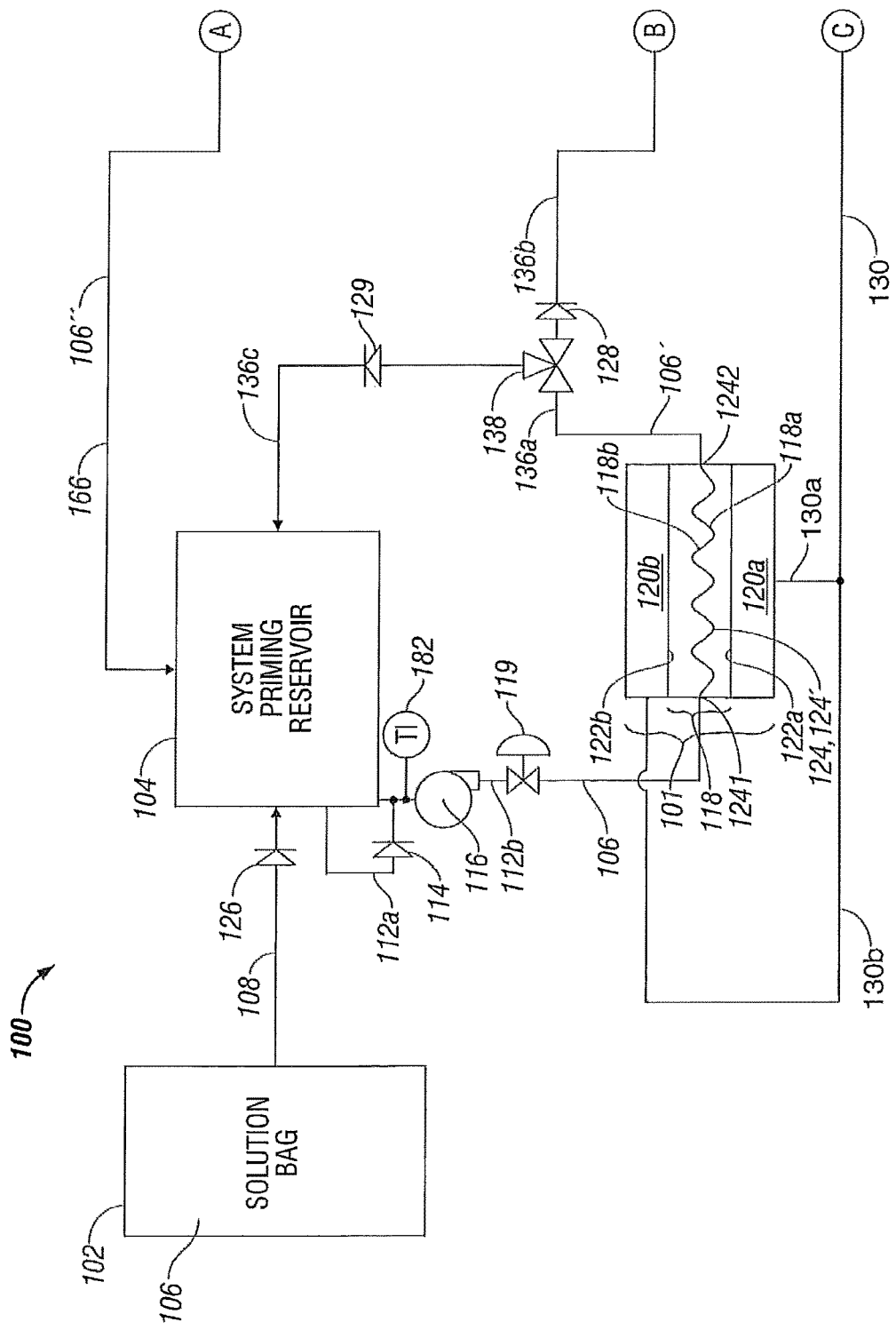
FIG. 1A is a portion of a schematic flow diagram of a system for controlling temperature of a fluid used during treatment of biological tissue according to one embodiment of the present disclosure that includes a heat transfer membrane cooled on more than one surface by at least one heat transfer device at each surface.
Figure 1B:
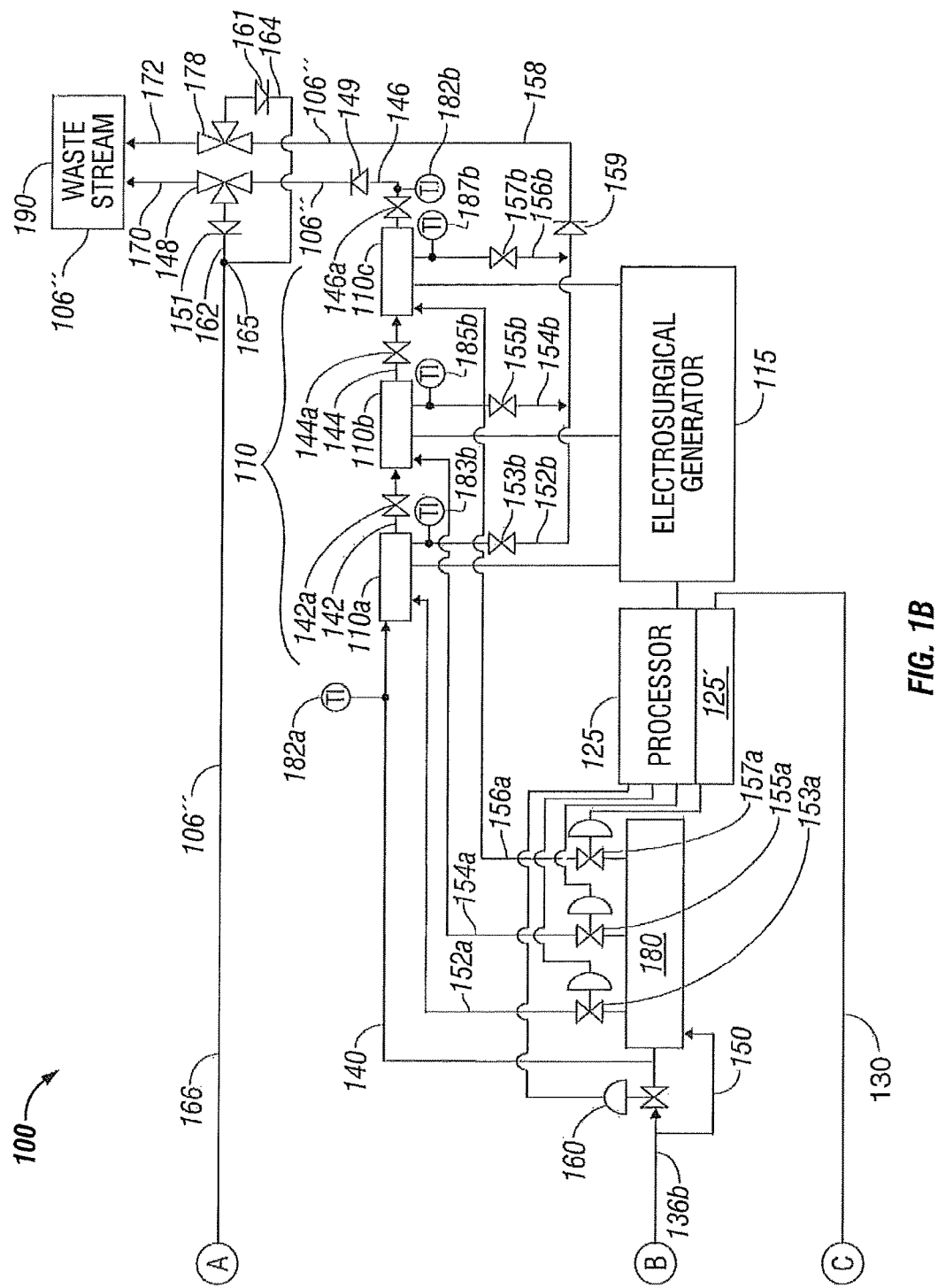
FIG. 1B is a continuation of the schematic flow diagram of a system for controlling temperature of a fluid of FIG. 1A.

Referring to FIGS. 1A-1B, there is illustrated a system 100 for controlling temperature of a fluid used during treatment of biological tissue according to an embodiment of the present disclosure. More particularly, temperature control system 100 includes a fluid temperature control apparatus 101. The fluid temperature control apparatus 101 includes a heat transfer membrane 118 having a first heat transfer surface 118 a and, in one embodiment, a second heat transfer surface 118 b. A fluid conduit 124 defines a path 124' through the first and second heat transfer surfaces 118 a and 118 b, respectively, of the heat transfer membrane 118. In the embodiment illustrated in FIG. 1A, the fluid conduit 124 defines a serpentine path 124' through the one or more heat transfer surfaces 118 a and 118 b of the heat transfer membrane 118. The fluid conduit 124 defines at least one fluid inlet connection 1241 and at least one fluid outlet connection 1242 to enable flow of fluid through the fluid conduit 124. The fluid conduit 124 is configured to enable heat transfer across the first and second heat transfer surfaces 118 a and 118 b, respectively, of the heat transfer membrane 118 upon flow of fluid through the fluid conduit 124 in the path 124'. The heat transfer membrane 118 is fluidically coupled to an electrosurgical device, e.g. electrosurgical device 110, and supplies fluid to the electrosurgical device 110 at a controlled temperature during a surgical procedure utilizing the electrosurgical device 110 to enable more efficient treatment of the biological tissue.

Heat transfer membrane 118 is in thermal communication with one or more heat transfer devices, e.g., first and second heat transfer devices 120 a and 120 b. More particularly, the first heat transfer device 120 a includes a heat transfer surface 122 a that resides in thermal communication with, or is in thermal communication with, the first heat transfer surface 118 a of the heat transfer membrane 118. Similarly, second heat transfer device 120 b includes a heat transfer surface 122 b that resides in thermal communication with, or is in thermal communication with, the second heat transfer surface 118 b of the heat transfer membrane 118.

In one embodiment, to be described in more detail below, the first and/or second heat transfer devices 120 a and 120 b, respectively, may be forced convection heat transfer devices that include a thermoelectric material. Alternatively, the first and/or second heat transfer devices 120 a and 120 b may be free convection heat transfer devices (e.g., passive such as an ice bath or ice).

The system 100 also includes a fluid supply reservoir 102, e.g., a saline solution bag or pouch configured to hold a volume of fluid 106, e.g., saline solution, sterile water or other biologically compatible fluid, used during treatment of biological tissue. The fluid supply reservoir 102 is in fluidic communication with a system priming reservoir 104 via at least one fluid conduit 108 that conveys the fluid 106 from the fluid supply reservoir 102 to the system priming reservoir 104. The fluid conduit 108 may include a check valve 126 that prevents reverse flow from the system priming reservoir 104 back to the solution bag 102.

System priming reservoir 104 is in fluidic communication with heat transfer membrane 118 that is, in turn, in thermal communication with the first heat transfer surface 122 a of the fluid temperature control apparatus 101. The system priming reservoir 104 is fluidically coupled to the heat transfer membrane 118 via a pump 116 that has a suction side fluid conduit 112 a that is coupled to the system priming reservoir 104 and a discharge side fluid conduit 112 b that is coupled to the heat transfer membrane 118. To prevent reverse flow through the pump 116, either the pump discharge side fluid conduit 112 b contains a check valve (not shown) or the pump suction side fluid conduit 112 a contains a check valve 114. The pump 116 conveys the fluid 106 from the system priming reservoir 104 to the membrane 118 and thus across at least one of the first and second heat transfer devices 120 a and 120 b, respectively.

The fluid 106 is pumped by the pump 116 through the heat transfer membrane 118 where the fluid 106 is cooled by the operation of at least one of the heat transfer devices 120 a and/or 120 b and is then discharged from the heat transfer membrane 118 via a discharge fluid conduit 136 a. A three-way fluid supply valve 138 is disposed in the discharge fluid conduit 136 a to enable flow of now cooled fluid 106' in a direction towards an electrosurgical device 110, (e.g., an RF ablation device, as discussed in more detail below), via fluid conduit 136 b, and to alternatively enable flow of cooled fluid 106' back to the system priming reservoir 104 via fluid conduit 136 c. To assure flow of cooled fluid 106' to the electrosurgical device 110, a check valve 128 may be disposed in the fluid conduit 136 b to prevent reverse flow of fluid from the fluid conduit 136 b towards the system priming reservoir 104. In addition, a check valve 129 may be disposed in the fluid conduit 136 c to prevent reverse flow from the system priming reservoir 104 towards the three-way valve 138.

As illustrated in the embodiment of FIGS. 1A-1B, cooling fluid 106' is directed from three-way fluid supply valve 138 through fluid conduit 136 b to electrosurgical device 110 in a series configuration having first, second and third electrodes 110 a, 110 b and 110 c fluidically coupled in series. The electrodes 110 a, 110 b and 110 c are supplied electrical power via an electrosurgical generator 115. A temperature or flow control valve 160 is disposed in fluid conduit 136 b in fluidic communication with the fluid supply valve 138 and in series fluidic communication with the first electrode 110 a through fluid conduit 140. The first electrode 110 a communicates with the second electrode 110 b through fluid conduit 142 and the second electrode 110 c communicates with the third electrode 110 c through fluid conduit 144.

Cooled fluid 106' is thus conveyed through the first, second and third electrodes 110 a, 110 b and 110 c, respectively, and is discharged from the third electrode 110 c through a fluid conduit 146 that is in fluidic communication with a three-way fluid discharge valve 148. The fluid discharge valve 148 enables diversion of the now heated fluid 106" discharging from the electrodes 110 a, 110 b and 110 c to be diverted either back to the system priming reservoir 104 through fluid conduits 162 and 166 or alternatively to be discharged to waste stream 190 through fluid conduit 170. To prevent reverse flow in the fluid conduit 146, a check valve 149 may be disposed therein. Similarly, to prevent reverse flow in fluid conduit 162, a check valve 151 may be disposed therein.

In an alternate embodiment, isolation valves 142 a, 144 a and 146 a may be disposed in the fluid conduit tubes 142, 144 and 146, respectively, to enable cooling fluid 106' to be directed from three-way fluid supply valve 138 through fluid conduit 136 *b* in a fluid conduit bypass 150 of the temperature or flow control valve 160 to electrosurgical device 110 (e.g., alternate embodiment having a parallel configuration with first, second and third electrodes 110 *a*, 110 *b* and 110 *c* fluidically coupled in parallel). A valve manifold 180 is fluidically coupled to the three-way supply valve 138 via the fluid conduits 136 *b* and 150. The first electrode 110 *a* is now fluidically coupled to the valve manifold 180 through a fluid conduit 152 *a*, the second electrode 110 *b* fluidically couples to the valve manifold through a fluid conduit 154 *a*, and the third electrode 110 *c* fluidically couples to the valve manifold 180 through a fluid conduit 156 *a*. Since the temperature or flow control valve 160 is bypassed for the parallel cooling configuration, individual temperature or flow control valves 153 *a*, 155 *a* and 157 *a* are disposed in the fluid conduit 152 *a* that is in fluidic communication with the first electrode 110 *a*, in the fluid conduit 154 *a* that is in fluidic communication with the second electrode 110 *b*, and in the fluid conduit 156 *a* that is in fluidic communication with the third electrode 110 *c*, respectively.

With isolation valves 142 *a*, 144 *a* and 146 *a* in a closed position, flow of now heated cooling fluid 106" is now established in a parallel configuration via the heated cooling fluid 106" being discharged from first electrode 110 *a* through a fluid conduit 152 *b* in fluid communication with flow control valve 153 *a* for the first electrode 110 *a*. In addition, the heated cooling fluid 106" is discharged from second electrode 110 *b* through a fluid conduit 154 *b* in fluid communication with flow control valve 155 *a* for the second electrode 110 *b* and the heated cooling fluid 106" is discharged from third electrode 110 *c* through a fluid conduit 156 *b* in fluid communication with flow control valve 157 *a* for the third electrode 110 *c*. The fluid conduits 152 *b*, 154 *b* and 156 *b* may each include discharge flow control valves 153 *b*, 155 *b* and 157 *b*, respectively, that, as shown, are manually-operated isolation valves. The fluid conduits 152 *b*, 154 *b* and 156 *b* discharge into a common discharge header or fluid conduit 158 that is, in turn, fluidically coupled to a three-way fluid discharge valve 178 for the parallel cooling fluid configuration of the electrosurgical instrument 110. In a similar manner as fluid discharge valve 148, the fluid discharge valve 178 enables diversion of the now heated fluid 106" discharging from the electrodes 110 *a*, 110 *b* and 110 *c* to be diverted either back to the system priming reservoir 104 through fluid conduit 164 (fluidically coupled to fluid conduit 162 at junction 165) that joins fluid conduit 166 and continues to the system priming reservoir 104 or, alternatively, the heated fluid 106" is discharged to waste stream 190 through fluid conduit 172. Again, to prevent reverse flow in the fluid conduit 158, a check valve 159 may be disposed therein. Similarly, to prevent reverse flow in fluid conduit 164, a check valve 161 may be disposed therein.

The temperature control system 100 may also include one or more sensors at various suitable locations, e.g., temperature sensors. For example, a temperature sensor 182 may be disposed in fluid conduit 112 *a* at the outlet of the system priming reservoir 104 on the suction side of pump 116. Temperature sensors 182 *a* and 182 *b* may be disposed proximate the electrosurgical device 110 in fluid conduit 140 at the inlet of first electrode 110 *a* and in fluid conduit 146 at the outlet of third electrode 110 *c* to provide temperature indication for the series cooling configuration of the electrodes 110 *a*, 110 *b* and 110 *c*.

To provide temperature indication for the parallel cooling configuration of the electrodes 110 *a*, 110 *b* and 110 *c*, temperature sensors 183 *b*, 185 *b* and 187 *b* may be disposed in the fluid conduits 152 *b*, 154 *b* and 156 *b* that discharge into the common discharge header or fluid conduit 158.

Processor 125 may include a controller 125' incorporated within the internal circuitry of the processor 125 (as shown), or a controller that may be a separate entity (not shown) that is in communication with the processor 125, that is disposed in operative communication with the sensors 182, 182 *a* and 182 *b* or with the sensors 183 *b*, 185 *b* and 187 *b* and with the fluid temperature control apparatus 101 to regulate the temperature of the fluid supplied to the electrodes 110 *a*, 110 *b* and 110 *c* during surgery to enable more efficient tissue treatment. The processor 125 and controller 125' are in electrical communication with the heat transfer devices 120*a* and 120*b* via a common electrical communication path 130 that branches into individual electrical communication path 130*a* to heat transfer device 120*a* and individual electrical communication path 130*b* to heat transfer device 120*b*. The temperature of the fluid is regulated by modulation of temperature control valve 160 for the series configuration of electrodes 110 *a*, 110 *b* and 110 *c* and by modulation of the individual temperature control valves 153 *a*, 155 *a* and 157 *a* for the first, second and third electrodes 110 *a*, 110 *b*, and 110 *c*, respectively, for the parallel configuration of the electrodes. The sensors 182, 182 *a* and 182 *b* and the sensors 183 *b*, 185 *b* and 187 *b* are in communication with processor 125. The processor 125 is also in communication with the electrosurgical generator 115 and with the temperature control valves 160 and 153 *a*, 155 *a* and 157 *a* to control the system 100 to regulate the temperature of the fluid 106. The sensors 182, 182 *a* and 182 *b* and the sensors 183 *b*, 185 *b* and 187 *b* thus may be disposed in operative communication with the fluid conduits 140 and 146 relative to the electrosurgical device 110 at a position that is either proximal, e.g., sensor 182 *a*, or distal, e.g., sensor 182 *b* or 183 *b*, 185 *b* and 187 *b*, to the electrosurgical device 110. As described above, the fluid 106 may be transferred as waste fluid 106" to waste stream (or sink) 190 or may be returned to the system priming reservoir 104.

Figure 1C:
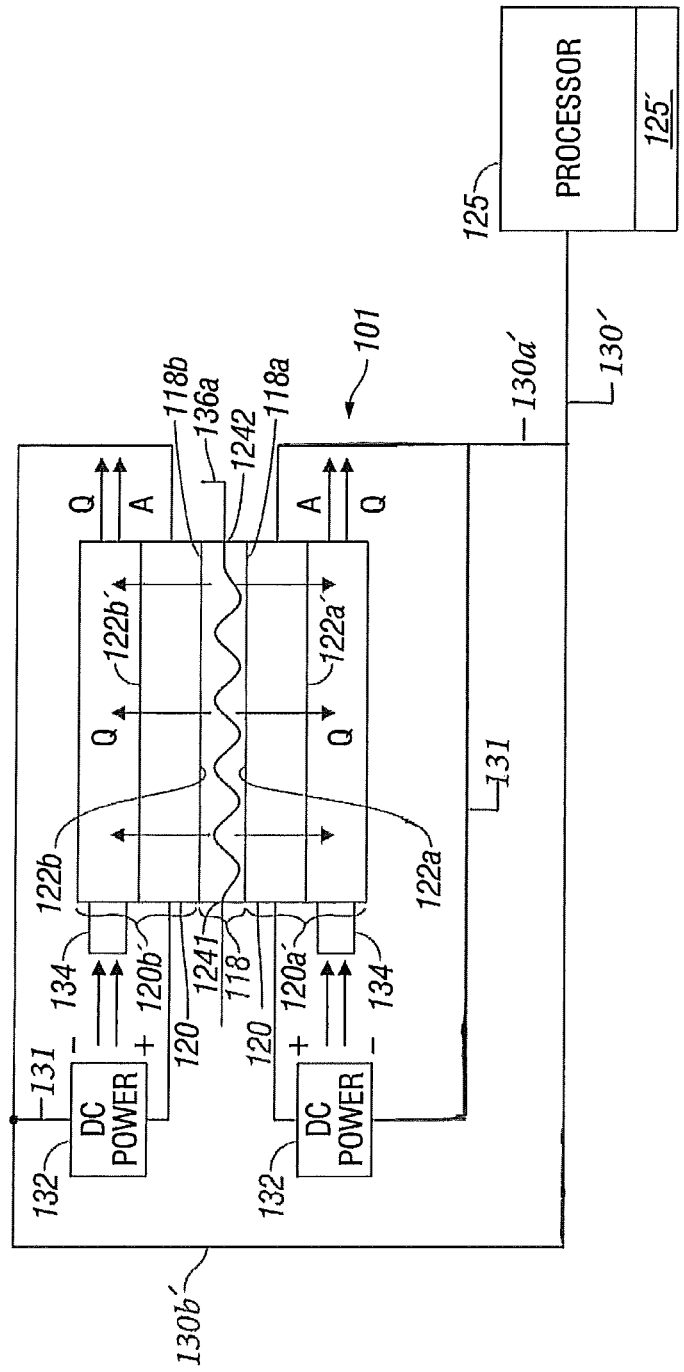
FIG. 1C is a schematic diagram illustrating details of first and second thermoelectric coolers that are configured to act as heat transfer devices that cool the heat transfer membrane of FIG. 1A on more than one surface.

Turning now to FIG. 1C, there is illustrated an exemplary embodiment of the present disclosure wherein the fluid temperature control apparatus 101 includes one or more heat transfer devices 120 *a*, 120 *b* that act as thermoelectric coolers each having a thermoelectric material 120 that is configured with a surface that forms the heat transfer surface 122 *a* of first heat transfer device 120 *a* or second heat transfer surface 122 *b* of heat transfer device 120 *b*'. The thermoelectric material 120 thermally communicates with, and in particular may be in direct contact with, the first and second heat transfer surfaces 118 *a*, 118 *b*, respectively, of the heat transfer membrane 118. The processor 125 and controller 125' are in electrical communication with the heat transfer devices 120*a*' and 120*b*' via a common electrical communication path 130' that branches into individual electrical communication path 130*a*' to heat transfer device 120*a*' and individual electrical communication path 130*b*' to heat transfer device 120*b*'. Via branch connections 131 from individual electrical communication paths 130*a*' and 130*b*' to power supplies 132 that supply direct current to the thermoelectric material 120, upon application of electrical power, to the thermoelectric material 120, heat Q is transferred from heat transfer surface 122 *a* to a second heat transfer surface 122 *a*' formed by the thermoelectric material 120 of the first heat transfer device 120 *a* and from heat transfer surface 122 *b* to a second heat transfer surface 122 *b*' formed by the thermoelectric material of the second heat transfer device 120*b*. In the case of forced convection cooling, a fan 134 may be disposed in fluidic communication with the thermoelectric material 120 to cause an air flow A to transfer heat Q from the second heat transfer surfaces 122 a', 122 b' to the surrounding air. The thermoelectric coolers 120 a', 120 b' thus include the thermoelectric material 120 and the electric power supply 132 and the fan 134.

In one embodiment, the fluid temperature control apparatus 101 includes at least one of, in addition to, or in place of, the thermoelectric cooler 120 a', 120 b', an evaporative cooler (not shown) and a gas expansion cooler (not shown).

Returning again to FIGS. 1A-1B, in one embodiment, fluid flow rate controller 119, e.g., a flow control valve, that regulates the flow rate of fluid 106 flowing from the fluid conduit 108 and the system priming reservoir 104 is disposed in the fluid conduit 112 b on the discharge side of pump 116. In one embodiment, the cooling temperature of the fluid 106 is regulated based on the sensed data from the temperature sensors 182, 182 a, 182 b and/or 183 b, 185 b, 187 b by adjusting the flow rate via the flow rate controller 119 or the electrical current supplied to the thermoelectric material 120 via electrical power supply 132 (see FIG. 1C).

In one embodiment, the system 100 includes a suitable algorithm that controls the flow rate of the fluid 106 through the fluid conduit 108 or 136 b and maximizes the cooling effect of the fluid 106 to enable more efficient tissue treatment. In another embodiment, the algorithm is associated with, or resides in the processor 125, and more particularly may reside in the controller 125'. In one embodiment, the temperature of the cooling fluid 106' exiting the fluid temperature control apparatus 101 and directed toward the electrosurgical device 110 (e.g., ablation electrodes 110 a, 110 b, 110 c) is in the range of about 0.1 degree Celsius to about 10 degrees Celsius.

When the system 100 is in a closed configuration, e.g., no fluid 106" is being discharged through the waste stream 190, the processor 125, including the controller 125', directs the flow of cooled fluid 106' through the three-way valve 138 to the fluid return conduit 136 c to the system priming reservoir 104 until the fluid temperature control apparatus 101 has cooled the fluid 106' to a desired temperature range. Once the desired temperature range of the cooling fluid 106' has been achieved, the processor 125/controller 125' transfers the three-way valve 138 to a position so as to direct the fluid 106' through the fluid conduit 136 b to the electrosurgical device 110 as explained above. Upon exiting the electrosurgical device 110, the (now heated) fluid 106" is circulated back through the fluid conduit 166 to the system priming reservoir 104 and is pumped via the pump 116 to the fluid temperature control apparatus 101 where the heated fluid 106" is again cooled and returned to the electrosurgical device 110.

When the system 100 is in an open configuration, e.g., fluid 106" is being discharged through the waste stream 190 (such as to maintain sterility or for other reasons), fluid 106 is drawn from the solution bag 102 into the system 100 to maintain the level in the system priming reservoir 104. Once discharge through the waste stream 190 is ceased, operation of system 100 may either be ceased or returned to the closed configuration operation of cooling the electrosurgical device 110 as described above.

Figure 2A:
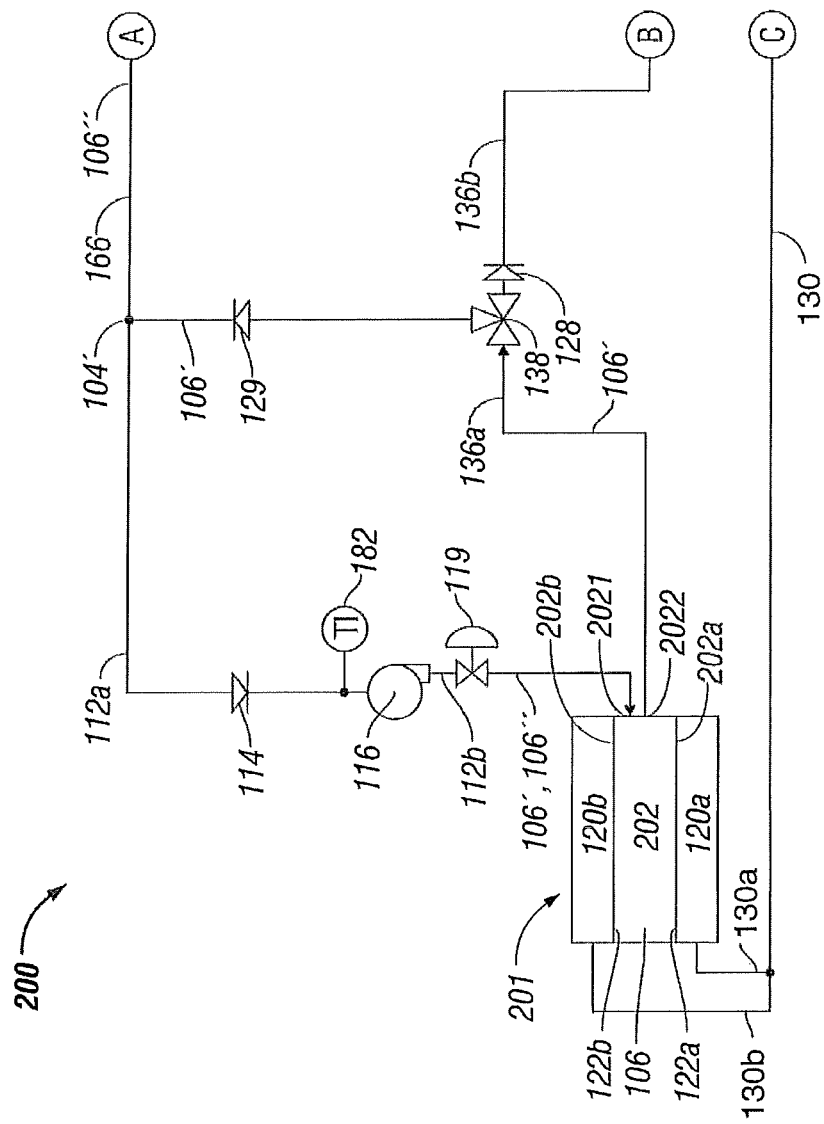
FIG. 2A is a portion of a schematic flow diagram of a system for controlling temperature of a fluid used during treatment of biological tissue according to one embodiment of the present disclosure that includes a solution bag cooled on more than one surface by at least one heat transfer device at each surface.
Figure 2B:
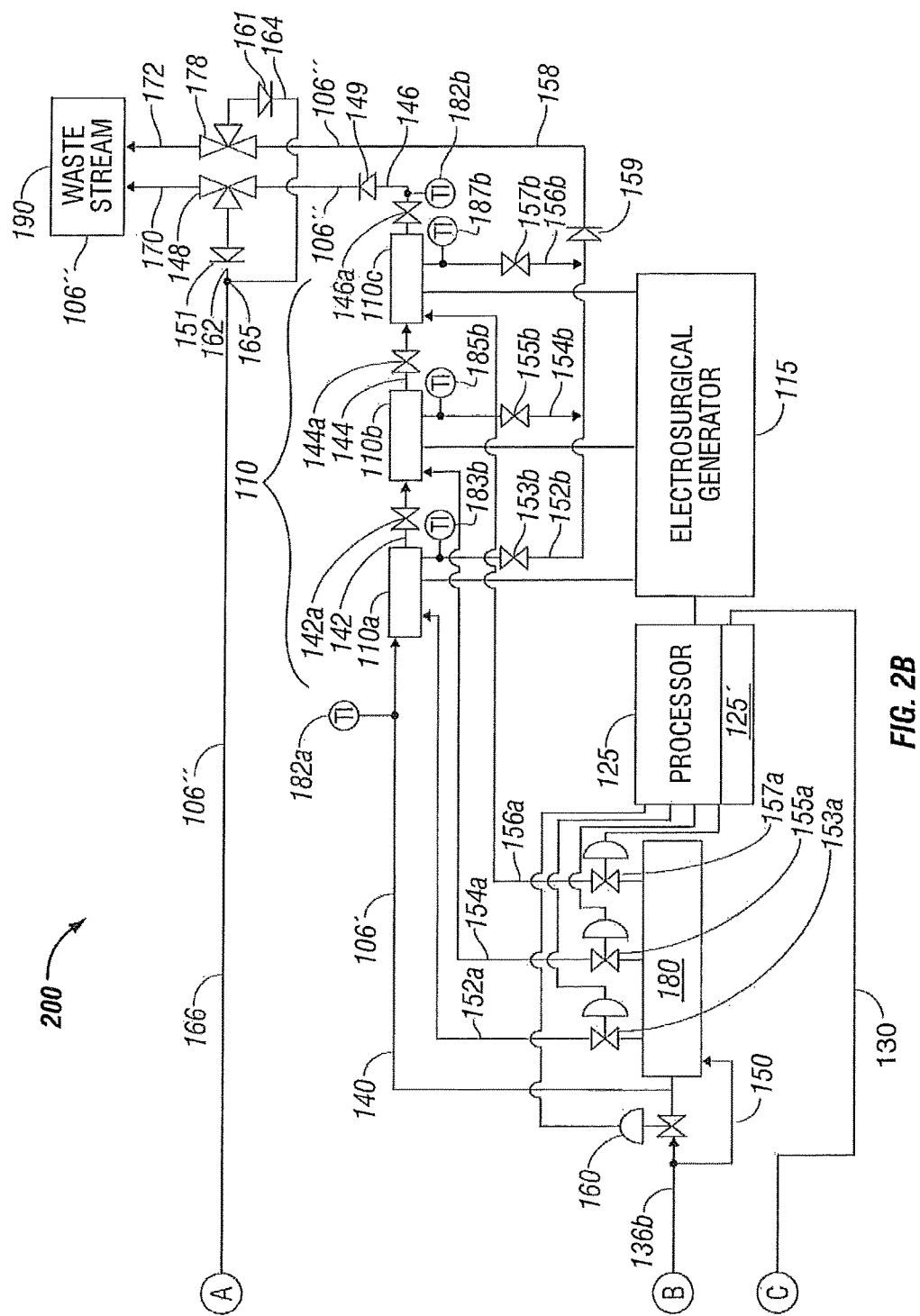
FIG. 2B is a continuation of the schematic flow diagram of a system for controlling temperature of a fluid of FIG. 2A.

FIGS. 2A-2B illustrate a system 200 for controlling temperature of a fluid used during treatment of biological tissue according to another embodiment of the present disclosure. More particularly, temperature control system 200 is substantially identical to temperature control system 100 described above with respect to FIGS. 1A-1B except that the solution bag 102 that supplies makeup fluid to system priming reservoir 104 and the system priming reservoir 104 are both omitted. In addition, the fluid conduit 166 that enables flow from the three-way valves 148 and 178 is now fluidically coupled, at junction 104', directly to suction side fluid conduit 112 a of pump 116. Consequently, for simplicity and brevity, to the extent possible, only those portions of system 200 that differ from system 100 are described herein.

In that regard, system 200 includes a fluid temperature control apparatus 201. The fluid temperature control apparatus 201 includes, in place of heat transfer membrane 118 having heat transfer surfaces 118 a and 118 b of fluid temperature control apparatus 101 of FIG. 1A, at least one solution bag 202, containing fluid 106 and has at least a first heat transfer surface 202 a and, in one embodiment, a second heat transfer surface 202 b. In a similar manner as described previously with respect to heat transfer membrane 118 illustrated in FIG. 1A, the solution bag 202 resides in thermal communication or is in thermal communication with one or more heat transfer devices 120 a, 120 b. The solution bag 202 includes a fluid inlet connection 2021 fluidically coupled to the fluid conduit 112 b at the discharge of pump 116 and a fluid outlet connection 2022 fluidically coupled to three-way valve 138 via fluid conduit 136 a, such that the fluid inlet connection 2021 and the fluid outlet connection 2022 enable fluidically coupling the solution bag 202 to the electrosurgical device 110, via the fluid conduit 136 a, to supply cooled fluid 106' to the electrosurgical device 110 in a similar manner as described above with respect to system 100 of FIGS. 1A-1B. In a similar manner as described above with respect to FIGS. 1A and 1B, the processor 125 and the controller 125' are in electrical communication with the heat transfer devices 120a and 120b via common electrical communication path 130 that branches into individual electrical communication path 130a to heat transfer device 120a and individual electrical communication path 130b to heat transfer device 120b. When the solution bag 202 is coupled to the electrosurgical device 110 to supply cooled fluid 106' thereto, the cooled fluid 106' is supplied to the electrosurgical device 110 at a controlled temperature during a surgical procedure utilizing the electrosurgical device 110 to enable more efficient treatment of the biological tissue.

In a similar manner, when the system 200 is in a closed configuration (e.g., no fluid 106" is being discharged through the waste stream 190) the processor 125, including the controller 125', directs the flow of cooled fluid 106' through the three-way valve 138 to the fluid return conduit 136 c to solution bag 202 through the pump 116, until the fluid temperature control apparatus 201 has cooled the fluid 106' to a desired temperature range. Once the desired temperature range of the fluid 106' has been achieved, the processor 125/controller 125' transfers the three-way valve 138 to a position so as to direct the fluid 106' through the fluid conduit 136 b to the electrosurgical device 110 as explained above. Upon exiting the electrosurgical device 110, the (now heated) fluid 106" is circulated back through the fluid conduit 166 to the pump 116 to the fluid temperature control apparatus 201 where the fluid 106" is again cooled and returned to the electrosurgical device 110.

When the system 200 is in an open configuration (e.g., fluid 106" is being discharged through the waste stream 190 (such as to maintain sterility or for other reasons)), fluid 106 is drawn from the solution bag 202 into the system 200 to maintain an adequate operating pressure and fluid volume for a period of time. As can be appreciated, solution bag 202 may contain a large volume of fluid 106 substantially sufficient to act in place of system priming reservoir 104 and solution bag 102 illustrated in FIG. 1A so as to maintain an adequate operating pressure and fluid volume for a period of time. Once discharge through the waste stream 190 is ceased, operation of system 200 may either be ceased or returned to the closed configuration operation of cooling the electrosurgical device 110 as described above.

Figure 3A:
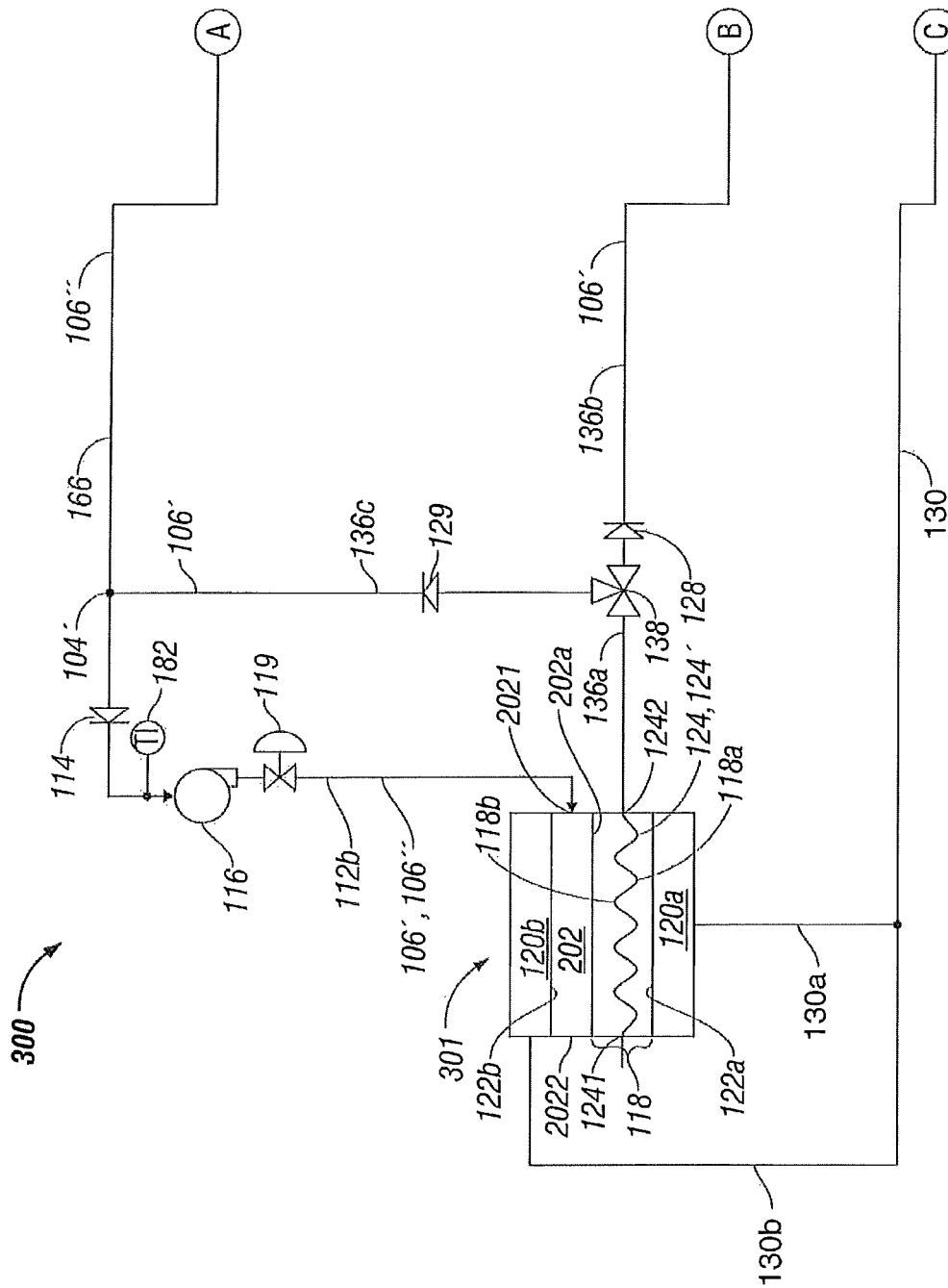
FIG. 3A is a portion of a schematic flow diagram of a system for controlling temperature of a fluid used during treatment of biological tissue according to one embodiment of the present disclosure that includes a solution bag that is in thermal contact with, and fluidically coupled to, a heat transfer membrane, wherein the solution bag and the heat transfer membrane are each cooled on one or more surfaces by one or more heat transfer devices.
Figure 3B:
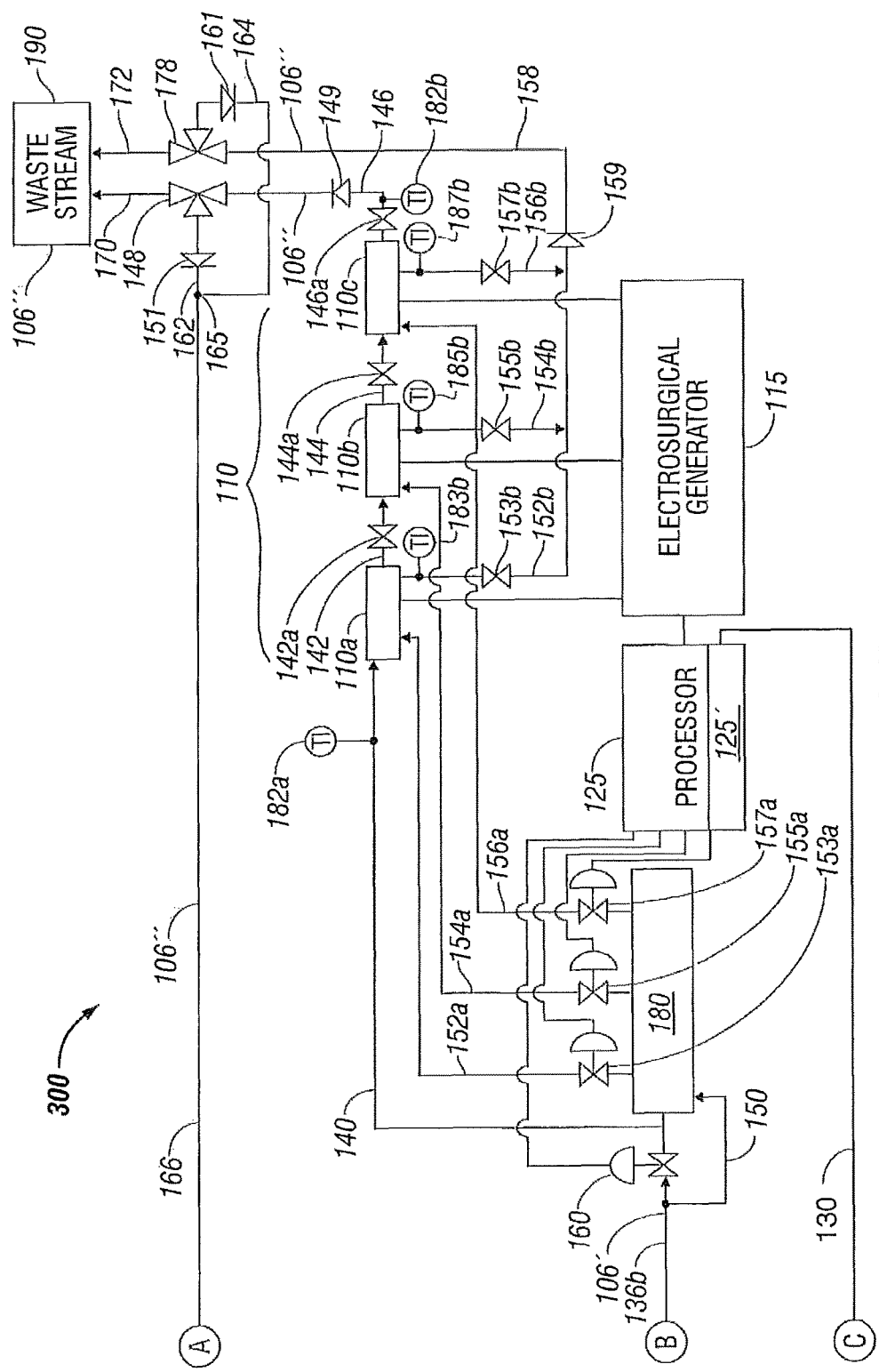
FIG. 3B is a continuation of the schematic flow diagram of a system for controlling temperature of a fluid of FIG. 3A.

FIGS. 3A-3B illustrate a system 300 for controlling temperature of a fluid used during treatment of biological tissue according to another embodiment of the present disclosure. Temperature control system 300 is substantially similar to temperature control system 200 described above with respect to FIGS. 2A-2B. Again, for simplicity and brevity, to the extent possible, only those portions of system 300 that differ from system 200 are described herein.

More particularly, system 300 includes a fluid temperature control apparatus 301 that includes solution bag 202, containing fluid 106, and having first and second heat transfer surfaces 202 a and 202 b, respectively, and the heat transfer membrane 118 having first and second heat transfer surfaces 118 a and 118 b, respectively. The solution bag 202 again is fluidically coupled, via fluid inlet connection 2021, to the discharge of pump 116 via fluid conduit 112 b. However, the solution bag 202 is fluidically coupled in series, via fluid outlet connection 2022, to the heat transfer membrane 118, via fluid inlet connection 1241. In turn, fluid outlet connection 1242 of heat transfer membrane 118 is fluidically coupled to the electrosurgical device 110 through the three-way valve 138 via the fluid conduit 136 a to enable fluidically coupling the solution bag 202 to the electrosurgical device 110.

In a similar manner as described previously with respect to solution bag 202 illustrated in FIG. 2A, the second heat transfer surface 202 b of solution bag 202 thermally communicates with the heat transfer surface 122 b of second heat transfer device 120 b. Similarly, the first heat transfer surface 118 a of heat transfer membrane 118 thermally communicates with heat transfer surface 122 a of first heat transfer device 120 a.

However, fluid system 300 differs from fluid systems 100 and 200 in that the first heat transfer surface 202 a of solution bag 202 thermally communicates with second heat transfer surface 118 b of heat transfer membrane 118.

Therefore, since the solution bag 202 and the heat transfer membrane 118 are fluidically coupled in series, both the solution bag 202 and heat transfer membrane 118 are thereby fluidically coupled to the electrosurgical device 110 to supply cooling fluid 106' thereto. Again, in a similar manner as described above with respect to FIGS. 1A and 1B, the processor 125 and the controller 125' are in electrical communication with the heat transfer devices 120a and 120b via common electrical communication path 130 that branches into individual electrical communication path 130a to heat transfer device 120a and individual electrical communication path 130b to heat transfer device 120b. Again, in this instance, the cooling fluid 106' is supplied to the electrosurgical device 110 at a controlled temperature during a surgical procedure utilizing the electrosurgical device 110 to enable more efficient treatment of the biological tissue.

In a similar manner, when the system 300 is in a closed configuration (e.g., no fluid 106" is being discharged through the waste stream 190) the processor 125, including the controller 125', directs the flow of cooling fluid 106' through the three-way valve 138 to the fluid return conduit 136 c to solution bag 202 and to the heat transfer membrane 118 (fluidically coupled in series to one another) through the pump 116. Fluid is directed in this manner until the fluid temperature control apparatus 301 has cooled the fluid 106' to a desired temperature range. Once the desired temperature range of the fluid 106' has been achieved, the processor 125/controller 125' transfers the three-way valve 138 to a position so as to direct the fluid 106' through the fluid conduit 136 b to the electrosurgical device 110 as explained above. Upon exiting the electrosurgical device 110, the (now heated) fluid 106" is circulated back through the fluid conduit 166 to the pump 116 to the fluid temperature control apparatus 301 where the fluid 106" is again cooled and returned to the electrosurgical device 110.

When the system 300 is in an open configuration, e.g., fluid 106" is being discharged through the waste stream 190 (such as to maintain sterility or for other reasons), fluid 106 is drawn from the solution bag 202, and through the heat transfer membrane 118, into the system 300 to maintain an adequate operating pressure and fluid volume. Once discharge through the waste stream 190 is ceased, operation of system 300 may either be ceased or returned to the closed configuration operation of cooling the electrosurgical device 110 as described above.

Figure 4A:
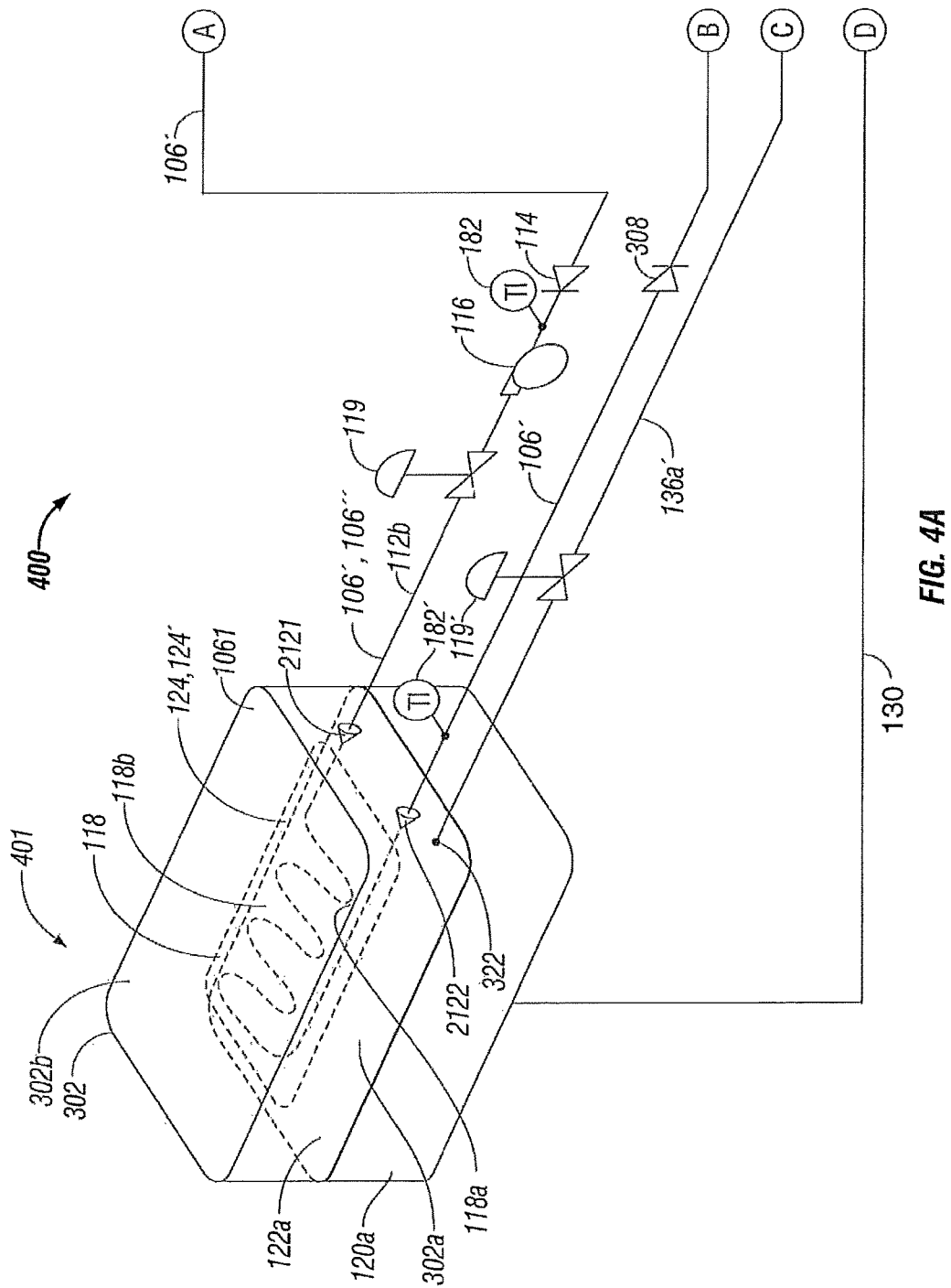
FIG. 4A is a portion of a schematic flow diagram of a system for controlling temperature of a fluid used during treatment of biological tissue according to one embodiment of the present disclosure that includes a heat transfer membrane enclosed internally within a solution bag wherein the solution bag is cooled on one or more surfaces by one or more heat transfer devices according to the present disclosure.
Figure 4B:
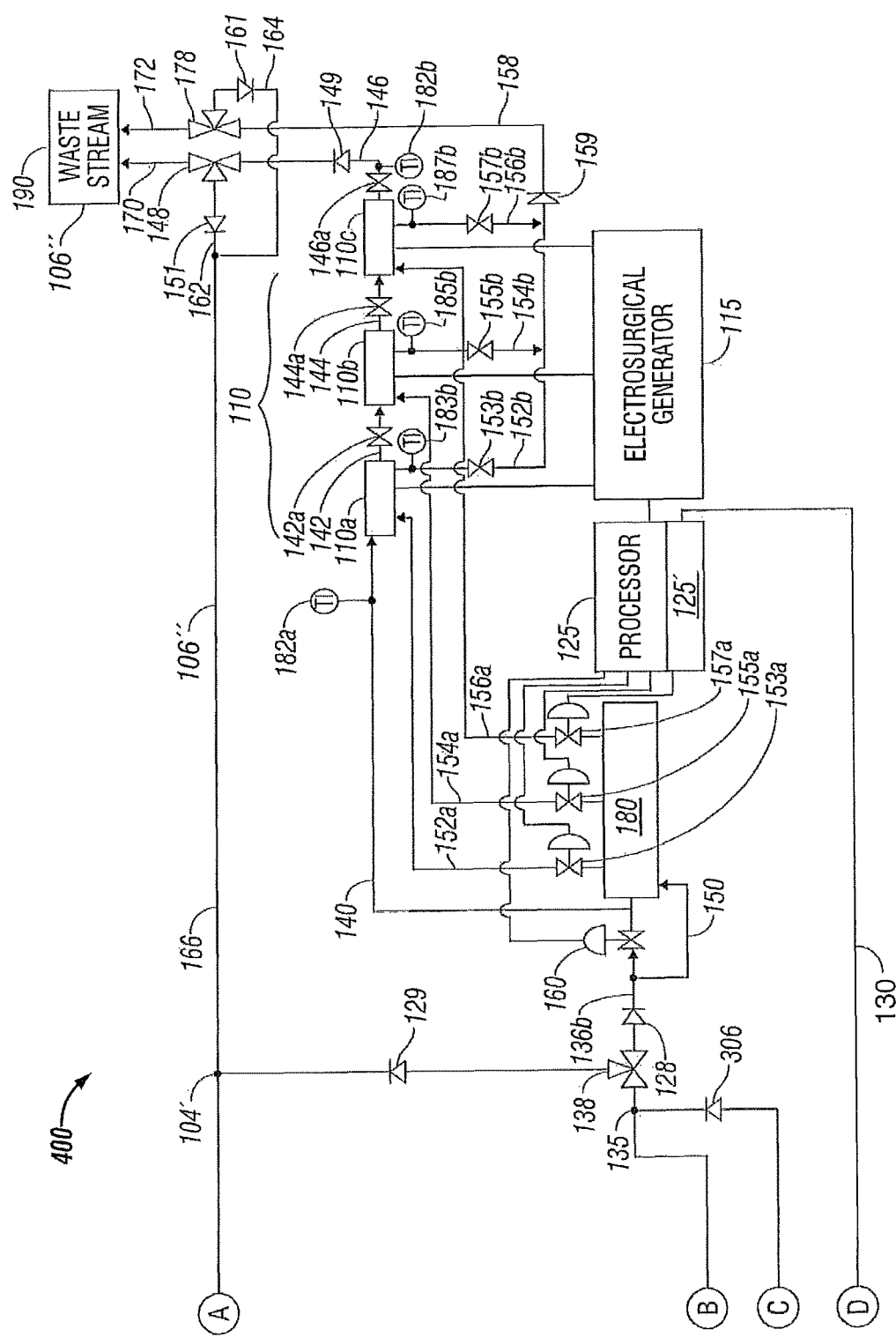
FIG. 4B is a continuation of the schematic flow diagram of a system for controlling temperature of a fluid of FIG. 4A.

FIGS. 4A-4B illustrate a system 400 for controlling temperature of a fluid used during treatment of biological tissue according to yet another embodiment of the present disclosure. Again, for simplicity and brevity, to the extent possible, only those portions of system 400 that differ from systems 100, 200 and 300 are described herein.

More particularly, system 400 includes a fluid temperature control apparatus 401 that includes one or more solution bags 302 containing fluid 106 and having at least a first external heat transfer surface 302 a and, in one embodiment, a second external heat transfer surface 302 b. The solution bag 302 differs from solution bags 102 and 202 in that the solution bag 302 is configured to receive at least one heat transfer membrane 118 internally therewithin to enable thermal communication of fluid 1061 contained within the solution bag 302 with at least one heat transfer surface, e.g., first heat transfer surface 118 a. Again, fluid conduit 124 defines path 124' through the first and second heat transfer surfaces 118 a and 118 b, respectively, of the heat transfer membrane 118.

The fluid conduit 124 defines a fluid inlet connection 2121 for the heat transfer membrane 118 in the solution bag 302 that is common with the fluid inlet connection to the solution bag 302. Similarly, the fluid conduit 124 defines a fluid outlet connection 2122 for the heat transfer membrane 118 in the solution bag 302 that is common with the fluid outlet connection from the solution bag 302. In a similar manner as with respect to fluid system 100 described above with respect to the heat transfer membrane 118 of FIG. 1A, the heat transfer membrane 118 again is fluidically coupled, via fluid inlet connection 2121, to the discharge of pump 116 via fluid conduit 112 b. Also in a similar manner as with respect to fluid system 100 described above with respect to the heat transfer membrane 118 of FIG. 1A, the heat transfer membrane 118 fluidically couples, via fluid outlet connection 2122, to the electrosurgical device 110 through the three-way valve 138 via the fluid conduit 136 a to enable fluidically coupling the heat transfer membrane 118, internally disposed within the solution bag 302, to the electrosurgical device 110 to enable more efficient treatment of the biological tissue. In a similar manner as described above with respect to FIGS. 1A-1B, 2A-2B and 3A-3B, the processor 125 and the controller 125' are in electrical communication with the heat transfer device 120a via electrical communication path 130.

The cooling fluid 106, traveling through the fluid conduit 124 of the heat transfer membrane 118 and the fluid 1061 contained within the solution bag 302 are physically isolated from, but in thermal communication with, one another through the first and second heat transfer surfaces 118 a and 118 b, respectively. In one embodiment, the solution bag 302 further includes a fluid conduit 136 a' that is fluidically coupled at fluid outlet connection 322 to enable flow of fluid 1061 from the solution bag 302 to the electrosurgical device 110 by a connection to fluid conduit 136 a at junction 135 upstream of the three-way valve 138. The fluid conduit 136 a' may further include a remotely controlled isolation valve 119' that may be controlled by the processor 125 (and controller 125') to enable the fluid 1061 within the solution bag 302 to be discharged into the system 400. The fluid conduit 136 a' may also include a check valve 306 to prevent undesired reverse flow from the fluid system 400 back into the solution bag 302. In addition, the fluid conduit 136 a from the fluid outlet connection 2122 to the three-way valve 138 may also include a check valve 308 to prevent undesired reverse flow from the solution bag 302 back into the fluid path 124' of the heat transfer membrane 118, although the same function is served by check valve 114 on the suction side of the pump 116.

Since the heat transfer membrane 118 (disposed internally within the solution bag 302) is fluidically coupled to the electrosurgical device 110 to supply cooling fluid 106' thereto, the fluid 106' is supplied to the electrosurgical device 110 at a controlled temperature during a surgical procedure utilizing the electrosurgical device 110 to enable more efficient treatment of the biological tissue.

In a similar manner as with respect to systems 100, 200 and 300, when the system 400 is in a closed configuration, e.g., no fluid 106" is being discharged through the waste stream 190, the processor 125, including the controller 125', directs the flow of fluid 106" through the three-way valve 138 to the fluid return conduit 136 c and to the heat transfer membrane 118 (disposed internally within the solution bag 302) through the pump 116. The fluid 106" flows in this manner until the fluid temperature control apparatus 401 has cooled the fluid 106" to a desired temperature range to form thereby cooling fluid 106'. Once the desired temperature range of the cooling fluid 106' has been achieved, the processor 125/controller 125' transfers the three-way valve 138 to a position so as to direct the fluid 106' through the fluid conduit 136 b to the electrosurgical device 110 as explained above. Upon exiting the electrosurgical device 110, the (now heated) fluid 106" is circulated back through the fluid conduit 166 to the pump 116 to the fluid temperature control apparatus 401 where the fluid 106" is again cooled and returned to the electrosurgical device 110.

Again, when the system 400 is in an open configuration (e.g., fluid 106" is being discharged through the waste stream 190 (such as to maintain sterility or for other reasons)), fluid 1061 may be drawn from the solution bag 302 through the fluid conduit 136 a' into the system 400 to maintain an adequate operating pressure and fluid volume. Once discharge through the waste stream 190 is ceased, operation of system 400 may either be ceased or returned to the closed configuration operation of cooling the electrosurgical device 110 as described above.

Those skilled in the art will recognize that a second heat transfer device, e.g., heat transfer device 120 b, illustrated in FIGS. 1, 2 and 3, may be disposed in thermal communication with the second heat transfer surface 302 b of the solution bag 302.

Figure 5A:
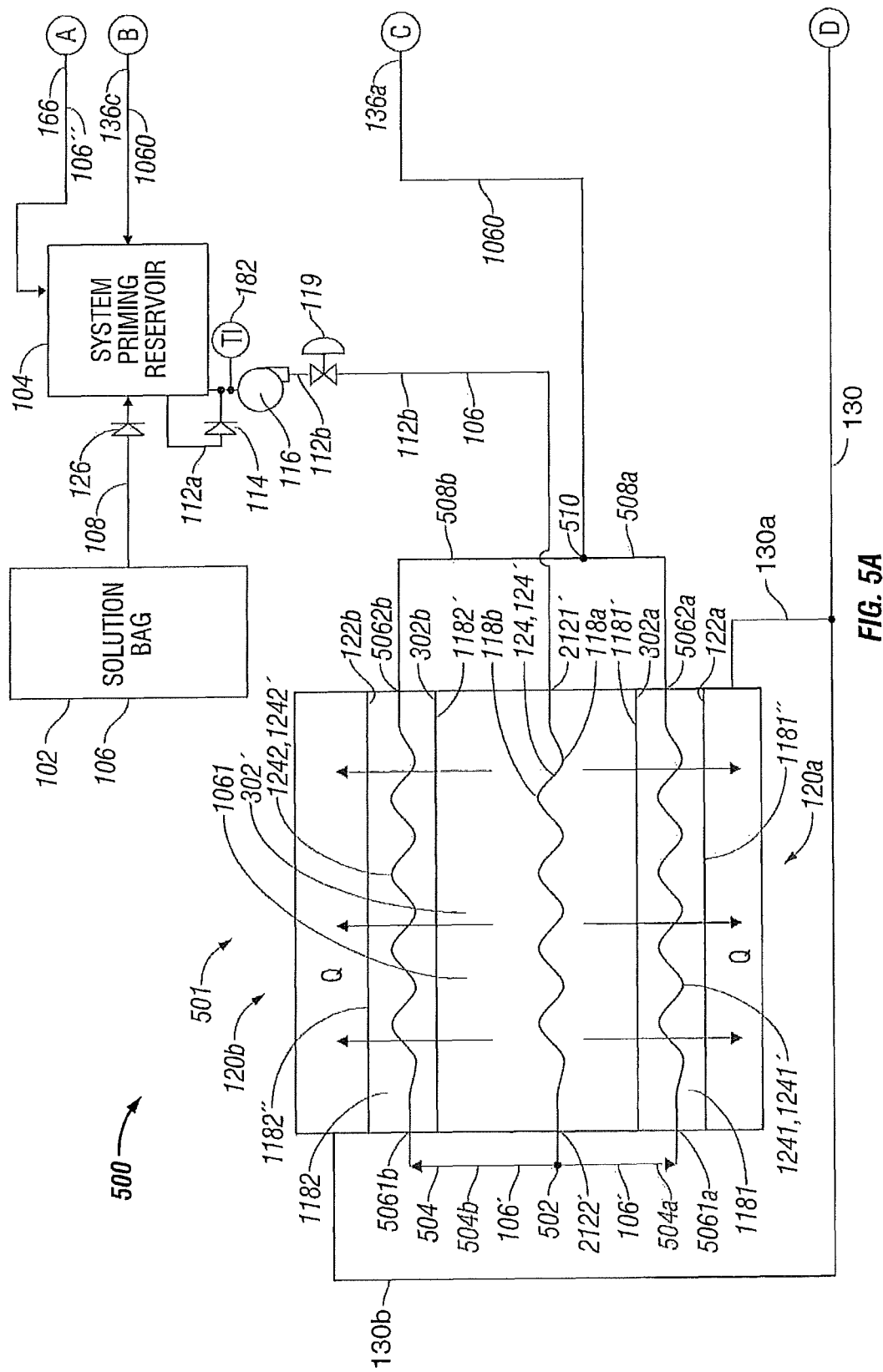
FIG. 5A is portion of a schematic flow diagram of a system for controlling temperature of a fluid used during treatment of biological tissue according to one embodiment of the present disclosure that includes a heat transfer membrane enclosed internally within a solution bag wherein the solution bag is cooled on one heat transfer surface by a first heat transfer membrane and is cooled on another heat transfer surface by a second heat transfer membrane and wherein the first heat transfer membrane is cooled by a heat transfer device and wherein the second heat transfer membrane is cooled by another heat transfer device.
Figure 5B:
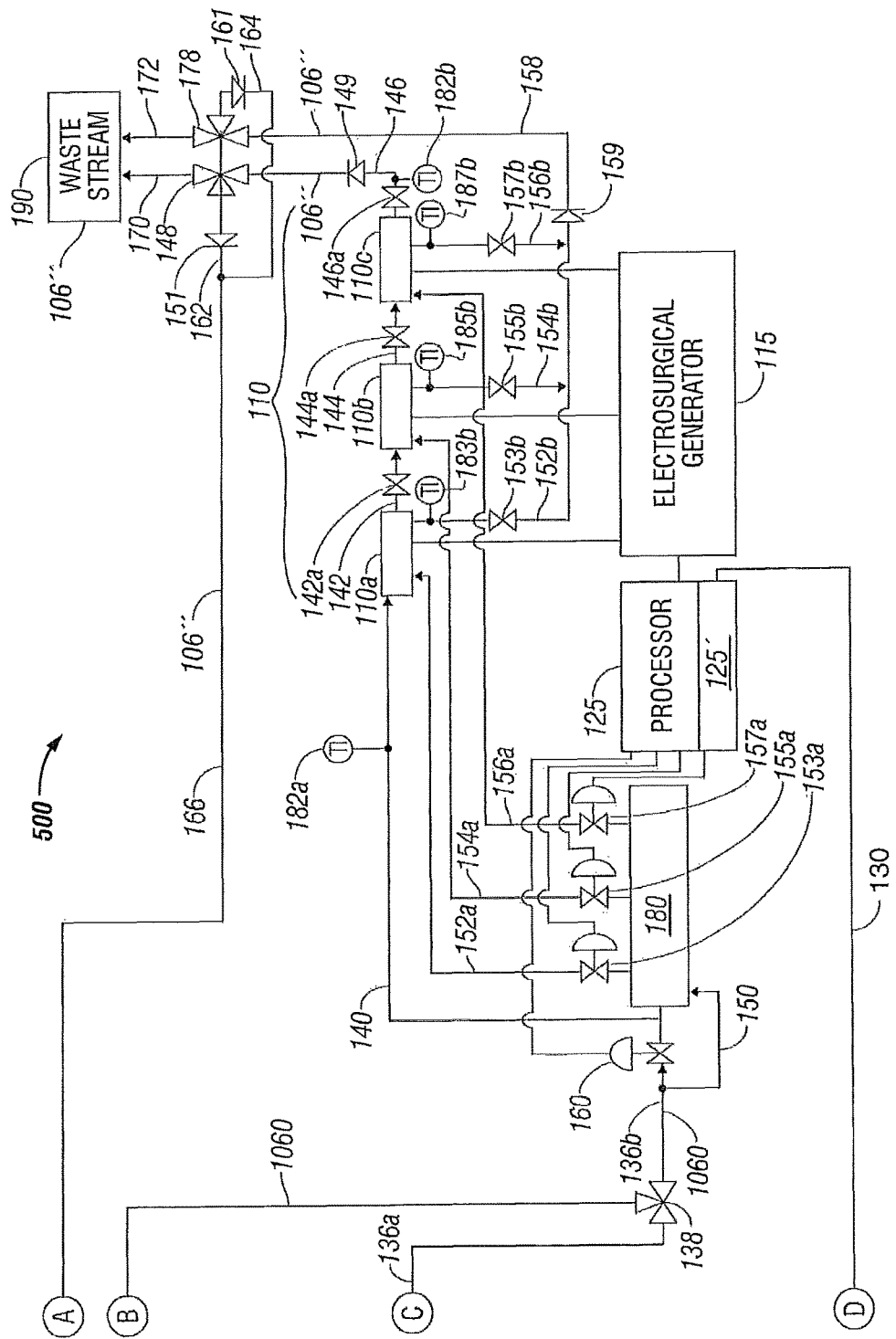
FIG. 5B is a continuation of the schematic flow diagram of a system for controlling temperature of a fluid of FIG. 5A.

FIGS. 5A-5B illustrate a system 500 for controlling temperature of a fluid used during treatment of biological tissue according to still another embodiment of the present disclosure. Temperature control system 500 is generally a combination of the temperature control systems 100, 200, 300 and 400 of FIGS. 1A-4B, respectively. Again, for simplicity and brevity, to the extent possible, only those portions of system 500 that differ from systems 100, 200, 300 and 400 are described herein.

More particularly, system 500 includes a fluid temperature control apparatus 501 that includes at least one solution bag 302' containing fluid 1061, as described above with respect to solution bag 302 of fluid temperature control apparatus 401. Solution bag 302' differs from solution bag 302 in that in place of fluid inlet and outlet connections 2121 and 2122, respectively, to internally disposed heat transfer membrane 118 being located adjacent to one another, fluid inlet and outlet connections 2121' and 2122', respectively, to internally disposed heat transfer membrane 118' of solution bag 302' are located on opposing ends of the solution bag 302' to facilitate fluidic coupling to externally disposed first and second heat transfer membranes 1181 and 1182, respectively, as explained below. In a similar manner as described above with respect to solution bag 302, solution bag 302', containing fluid 1061, has at least first external heat transfer surface 302 a (in one embodiment, second external heat transfer surface 302 b). The solution bag 302' is configured to receive at least one heat transfer membrane 118' internally therewithin to enable thermal communication of fluid 1061 contained within the solution bag 302' with at least one heat transfer surface 302 a and/or 302 b. Again, fluid conduit 124 defines path 124' through first and second heat transfer surfaces 118 a and 118 b, respectively, of the internally disposed heat transfer membrane 118'. Fluid conduit 124 defines fluid inlet connection 2121' for the heat transfer membrane 118' in the solution bag 302' that is common with the fluid inlet connection to the solution bag 302'. Similarly, fluid conduit 124 defines fluid outlet connection 2122' for the heat transfer membrane 118' in the solution bag 302' that is common with the fluid outlet connection from the solution bag 302'.

In a similar manner as with respect to fluid system 100 described above with respect to the heat transfer membrane 118 of FIG. 1A, the heat transfer membrane 118' is fluidically coupled, via fluid inlet connection 2121', to the discharge of pump 116 via fluid conduit 112 b.

However, the heat transfer membrane 118' fluidically couples, via fluid outlet connection 2122', to first and second externally disposed heat transfer membranes 1181, 1182 that are disposed externally with respect to solution bag 302', respectively.

The first and second externally disposed heat transfer membranes 1181, 1182 include a first heat transfer surface 1181', 1182', that thermally communicates with the first and second heat transfer surfaces 302 a, 302 b of the solution bag 302', respectively. The first and second externally disposed heat transfer membranes 1181, 1182 include a second heat transfer surface 1181", 1182" that thermally communicates with heat transfer surfaces 122 a, 122 b of first and second heat transfer devices 120 a, 120 b, respectively.

Cooled fluid 106' is communicated from the fluid outlet connection 2122' of the fluid path 124 to a junction point 502 in fluid header 504 where the fluid header 504 branches into first and second header segments 504 a, 504 b, that fluidically couple at fluid inlet connections 5061 a, 5061 b, to fluid conduits 1241, 1242 that define a path 1241', 1242' through the first and second heat transfer surfaces 1181', 1182' and 1181", 1182", of the heat transfer membranes 1181, 1182, respectively. The fluid conduits 1241, 1242 convey the cooled fluid 106' through the heat transfer membranes 1181, 1182 to fluid outlet connections 5062 a, 5062 *b*, where the now further cooled fluid 1060 is communicated into first and second header segments 508 *a*, 508 *b* of a fluid header 508, respectively. The fluid header 508 branches at junction point 510 to fluidically couple with the three-way valve 138 via fluid conduit 136 *a*, as described previously, such that the fluid header 508 is fluidically coupled to the electrosurgical device 110 to supply cooled fluid 1060 thereto. The fluid 1060 is supplied to the electrosurgical device 110 at a controlled temperature during a surgical procedure utilizing the electrosurgical device 110 to enable more efficient treatment of the biological tissue, as explained in greater detail following. Again, in a similar manner as described above with respect to FIGS. 1A-1B, 2A-2B, 3A-3B and 4A-4B, the processor 125 and controller 125' are in electrical communication with the heat transfer devices 120*a* and 120*b* via common electrical communication path 130 that branches into individual electrical communication path 130*a* to heat transfer device 120*a* and individual electrical communication path 130*b* to heat transfer device 120*b*.

Thus the temperature control apparatus 501 is configured, including the fluid conduit 124, such that heat is transferred from cooled fluid 106' in the fluid conduit 124 through the first and second heat transfer surfaces 118 *a* and 118 *b*, respectively, of the internally disposed heat transfer membrane 118 to the fluid 1061 within the solution bag 302'. This first phase of cooling lowers the temperature of fluid 106 to thereby form the fluid 106' that has been subjected to the first phase of cooling. The heat is further transferred from the fluid 106' through the first heat transfer surface 302 *a* of the solution bag 302 (in thermal communication with the first heat transfer surface 1181' of the first externally disposed heat transfer membrane 1181). Heat is further transferred to the fluid 106' in fluid conduits 1241, 1242 that define paths 1241', 1242' through the first heat transfer surfaces 1181', 1182' of the heat transfer membranes 1181, 1182 to the second heat transfer surfaces 1181", 1182" in thermal communication with heat transfer surfaces 122 *a*, 122 *b* of first and second heat transfer devices 120 *a*, 120 *b*, wherein the heat Q is transferred to the environment via operation of the first and second heat transfer devices 120 *a*, 120 *b*, respectively, in a second phase of cooling that further lowers the temperature of fluid 106' to form the fluid 1060 that has been subjected to the second phase of cooling.

Thus, the fluid conduits 124, 1241 and 1242 are configured and dimensioned to enable heat transfer across the heat transfer surfaces 118 *a*, 118 *b* of the heat transfer membrane 118, heat transfer surfaces 1181', 1181" of the heat transfer membrane 1181, and heat transfer surfaces 1182', 1182" of the heat transfer membrane 1182 upon flow of fluid 106 through the fluid conduits 124, 1241 and 1242 in the paths 124', 1241' and 1242', respectively.

The solution bag 302' is configured to contain fluid 1061 therewithin, and is configured to receive at least one heat transfer membrane 118 therewithin to enable thermal communication of the fluid 1061 contained within the solution bag 302' with one or more heat transfer surfaces 118 *a* and 118 *b* of the heat transfer membrane 118.

In a similar manner as with respect to system 100, system 500 includes fluid supply reservoir 102, e.g., a saline solution bag or pouch configured to hold a volume of fluid 106, e.g., saline solution, sterile water or other biologically compatible fluid, used during treatment of biological tissue. The fluid supply reservoir 102 communicates with system priming reservoir 104 via at least one fluid conduit 108 that conveys the fluid 106 from the fluid supply reservoir 102 to the system priming reservoir 104. The fluid conduit 108 may include check valve 126 that prevents reverse flow from the system priming reservoir 104 back to the solution bag 102. The system priming reservoir 104 fluidically communicates with heat transfer membrane 118' that is in thermal communication with the first heat transfer surface 122 *a* of the fluid temperature control apparatus 101. The system priming reservoir 104 fluidically couples to the heat transfer membrane 118 via a pump 116 that has a suction side fluid conduit 112 *a* that is coupled to the system priming reservoir 104 and a discharge side fluid conduit 112 *b* that is coupled to the membrane 118'. To prevent reverse flow through the pump 116, either the pump discharge side fluid conduit 112 *b* contains a check valve (not shown) or the pump suction side fluid conduit 112 *a* contains a check valve 114. The pump 116 conveys the fluid 106 from the system priming reservoir 104 to the membrane 118' and thus across at least one of the first and second heat transfer devices 120 *a* and 120 *b*, respectively.

In a similar manner as with respect to fluid system 100 described above with respect to the heat transfer membrane 118 of FIG. 1A, the heat transfer membrane 118' fluidically couples, via fluid inlet connection 2121', to the discharge of pump 116 via fluid conduit 112 *b*. Also in a similar manner as with respect to fluid system 100 described above with respect to the heat transfer membrane 118 of FIG. 1A, the heat transfer membranes 118', 1181 and 1182 fluidically couple, via fluid outlet header 508, to the electrosurgical device 110 through the three-way valve 138 via the fluid conduit 136 *a* to enable more efficient treatment of the biological tissue.

Again, the fluid 106' traveling through the fluid conduit 124 of the heat transfer membrane 118 and the fluid 1061 contained within the solution bag 302' are physically isolated from, but in thermal communication with, one another through the first and second heat transfer surfaces 118 *a* and 118 *b*, respectively.

Since the heat transfer membrane 118' disposed internally within the solution bag 302' fluidically couples to the electrosurgical device 110 to supply cooled fluid 1060 thereto, the fluid 1060 is supplied to the electrosurgical device 110 at a controlled temperature during a surgical procedure utilizing the electrosurgical device 110 to enable more efficient treatment of the biological tissue.

In a similar manner as with respect to system 100, when the system 500 is in a closed configuration (e.g., no heated fluid 106" is being discharged through the waste stream 190) the processor 125, including the controller 125', directs the flow of heated fluid 106" through the three-way valve 138 to the fluid return conduit 136 *c*, and to the system priming reservoir 104, through the pump 116, until the fluid temperature control apparatus 501 has cooled the fluid 1060 to a desired temperature. Once the desired temperature range of the fluid 1060 has been achieved, the processor 125/controller 125' transfers the three-way valve 138 to a position so as to direct the fluid 1060 through the fluid conduit 136 *b* to the electrosurgical device 110 as explained above. Upon exiting the electrosurgical device 110, the (now heated) fluid 106" is circulated back through the fluid conduit 166 to the system priming reservoir 104 and then to the pump 116 to the fluid temperature control apparatus 501 where the fluid 106" is again cooled and returned to the electrosurgical device 110.

Again, when the system 500 is in an open configuration (e.g., fluid 106" is discharged through the waste stream 190 (such as to maintain sterility or for other reasons)), fluid 106 may be drawn from the solution bag 102 through the fluid conduit 108 into the system 500 via the system priming reservoir 104 to maintain an adequate operating pressure and fluid volume. Once discharge through the waste stream 190 is ceased, operation of system 500 may either be ceased or returned to the closed configuration operation of cooling the electrosurgical device 110 as described above.

In view of the foregoing description of systems 100, 200, 300, 400 and 500 with respect to FIGS. 1A-5B, respectively, those skilled in the art will recognize that the embodiments of the present disclosure relate to a method for controlling temperature of the fluid 106, 106', 1060 or 106" that is used during treatment of biological tissue, wherein the method includes the steps of fluidically coupling a fluid temperature control apparatus, e.g., temperature control apparatuses 101, 201, 301, 401 and 501, to electrosurgical device 110 to supply fluid thereto; and supplying fluid 106, 106' or 1060 to the electrosurgical device 110 at a controlled temperature during a surgical procedure utilizing the electrosurgical device 110 to enable more efficient treatment of the biological tissue. The method may include the step of establishing communication between 125 processor/controller 125' and the fluid temperature control apparatus, e.g., temperature control apparatuses 101, 201, 301, 401 and 501 such that the processor 125/controller 125' controls the temperature of the fluid 106, 106' or 1060 supplied to the electrosurgical device 110.

The step of fluidically coupling a fluid temperature control apparatus, e.g., temperature control apparatuses 101, 201, 301, 401 and 501, to electrosurgical device 110 to supply fluid 106, 106' or 1060 thereto may be performed by fluidically coupling at least one solution bag 202 or 302 or 302' and/or at least one heat transfer membrane 118, 1181 and/or 1182 to the electrosurgical device 110 to supply fluid thereto. The method may further include the steps of: enabling thermal communication between at least one heat transfer device, e.g., heat transfer device 102 a and/or 102 b and the one or more solution bags 202 or 302 or 302' and at least one heat transfer membrane, e.g., 118, 118', 1181 and/or 1182, to cause heat transfer between the heat transfer device 102 a and/or 102 b and the one or more solution bags 202 or 302 or 302' and/or at least one heat transfer membrane 118, 118', 1181 and/or 1182; and supplying fluid 106, 106' or 1060 to the electrosurgical device 110 at a controlled temperature during a surgical procedure utilizing the at least one electrosurgical device 110 to enable more efficient treatment of the biological tissue.

In one embodiment, the method includes the step of fluidically coupling at least one solution bag 202 or 302 or 302' to the one or more heat transfer membranes 118, 118', 1181 and/or 1182. This step may be performed by fluidically coupling one or more solution bags 202 or 302 or 302' to one or more heat transfer membranes 118, 1181 and/or 1182 in series (see FIG. 3), or alternatively, by thermally coupling one or more solution bags 202 or 302 or 302' to one or more heat transfer membranes 118', 1181 and/or 1182 in parallel (see FIG. 5).

As can be appreciated from FIGS. 3A-3B and 5A-5B, the method may further include the step of causing thermal communication between at least one heat transfer surface 202 a or 202 b of at least one solution bag 202 or 302 or 302' and at least one heat transfer surface 118 a, 118 b, and/or 1181', 1181", and/or 1182', 1182" of the at least one heat transfer membrane 118,118', 1181 and/or 1182, respectively.

The method may further include the steps of configuring at least one solution bag 302 to contain fluid 1061 therewithin, and configuring the solution bag 302 or 302' to receive at least one heat transfer membrane 118 or 118' therewithin to enable thermal communication of fluid 1061 contained within the solution bag 302 or 302' with the one or more heat transfer membranes 118 or 118', respectively.

The step of causing heat transfer between one or more heat transfer devices 120 a and/or 120 b and one or more solution bags 202 or 302 and/or at least one heat transfer membrane 118, 118', 1181 and/or 1182 may be performed wherein at least one heat transfer device 120 a and/or 120 b is a thermoelectric cooler 120' (see FIG. 1C).

Referring again to FIGS. 1A-5B, the present disclosure may also relate to systems for controlling temperature of a fluid used during treatment of biological tissue to enable more efficient tissue treatment, e.g., systems 100 through 500. In one embodiment, when serving as flow rate controllers, controllers 119 or 160 or 153 b, 155 b or 157 b cooperate with the electrosurgical generator 115 and with the corresponding controllers serving as temperature controllers, e.g., controllers 119 or 160 or 153 b, 155 b or 157 b via the processor 125 to cool each of the electrodes 110 a, 110 b and 110 c during electrosurgical activation.

In one embodiment, the electrodes 110 a, 110 b and 110 c may be configured to include a plurality of ablation electrodes and the fluid rate controller(s) 119 or 160 or 153 b, 155 b, or 157 b cooperate with the electrosurgical generator 115 to cool each of the series of electrodes 110 a, 110 b, 110 c as each of the electrodes 110 a, 110 b, 110 c is activated.

In one embodiment, the plurality of electrodes 110 a, 110 b, 110 c are activated in a sequential order and the fluid rate controller(s) 119 or 160 or 153 b, 155 b, or 157 b cooperates with the electrosurgical generator 115 to cool each of the series of electrodes 110 a, 110 b, 110 c as each of the electrodes 110 a, 110 b 110 c is activated.

As may be appreciated, the present disclosure described above relates to systems and methods for efficient cooling of fluids used during biological treatment of tissue. The present disclosure relates also to a solution bag for use during treatment of biological tissue wherein the solution bag includes a membrane defining a volume therein for housing at least one fluid path. The fluid path is disposed in a general, serpentine manner within the volume to enhance the rate of heat transfer for a given surface area.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A surgical system, comprising:
a surgical instrument;
a first thermoelectric heat transfer device;
a second thermoelectric heat transfer device;
a fluid supply reservoir configured to store a fluid and is in fluid communication with the surgical instrument via a first fluid conduit;
a heat transfer membrane in fluid communication with the fluid supply reservoir and disposed between the first thermoelectric heat transfer device and the second thermoelectric heat transfer device, the heat transfer membrane including a heat transfer surface and a second fluid conduit defined through the heat transfer membrane, the second fluid conduit configured to transfer heat across the heat transfer surface of the heat transfer membrane upon flow of the fluid from the fluid supply reservoir through the second fluid conduit;
a third fluid conduit interconnecting the second fluid conduit and the surgical instrument;
a fourth fluid conduit in fluid communication with the third fluid conduit and the fluid supply reservoir, such that the fluid from the heat transfer membrane is returnable directly to the fluid supply reservoir; and
a three-way valve interconnecting the second fluid conduit, the third fluid conduit, and the fourth fluid conduit.

2. The surgical system according to claim 1, further comprising:
a pump in fluid communication with the fluid supply reservoir configured to circulate the fluid through at least one of the surgical instrument or the heat transfer membrane.

3. The surgical system according to claim 2, wherein the surgical instrument includes a plurality of electrodes.

4. The surgical system according to claim 3, wherein the plurality of electrodes are fluidically coupled to a flow control valve and the pump.

5. The surgical system according to claim 4, further comprising at least one temperature sensor disposed in a fluid flow path between the fluid supply reservoir and the surgical instrument.

6. The surgical system according to claim 5, further comprising a controller coupled to the at least one temperature sensor and at least one of the first or second thermoelectric heat transfer devices.

7. The surgical system according to claim 6, wherein the controller is configured to adjust a heat transfer rate of the at least one of the first or second thermoelectric heat transfer devices to maintain a temperature of the fluid based on a measured temperature received from the at least one temperature sensor.

8. The surgical system according to claim 7, wherein the controller is coupled to the flow control valve.

9. The surgical system according to claim 8, wherein the controller is configured to adjust modulation of the flow control valve to maintain the temperature of the fluid based on the measured temperature received from the at least one temperature sensor.

10. The surgical system according to claim 1, further comprising a valve configured to selectively control recirculation of the fluid from the fourth fluid conduit to the fluid supply reservoir.

* * * * *